(12) United States Patent
Kim et al.

(10) Patent No.: US 6,440,297 B1
(45) Date of Patent: Aug. 27, 2002

(54) SYSTEM AND METHOD FOR DETERMINING NOBLE METAL CONCENTRATIONS IN REACTOR COOLANT STREAMS

(75) Inventors: Young Jin Kim, Clifton Park; John Yupeng Gui, Niskayuna; Peter Louis Andresen, Schenectady, all of NY (US); Thomas Pompilio Diaz, San Martin; Samson Hettiarachchi, Menlo Park, both of CA (US)

(73) Assignee: General Electric Company, Niskayuna, NY (US)

( * ) Notice: Subject to any disclaimer, the term of this patent is extended or adjusted under 35 U.S.C. 154(b) by 77 days.

(21) Appl. No.: 09/739,181

(22) Filed: Dec. 18, 2000

(51) Int. Cl.[7] ............................ G01N 27/26; G21C 17/01
(52) U.S. Cl. ...................... 205/791; 205/775; 204/400; 204/434; 376/249; 376/306
(58) Field of Search ................ 205/777.5, 776.5, 205/790, 790.5, 775, 791; 204/400, 404, 434; 376/249, 305, 306

(56) References Cited

U.S. PATENT DOCUMENTS

| | | | | |
|---|---|---|---|---|
| 4,132,605 A | * | 1/1979 | Tench et al. | 204/434 |
| 5,171,517 A | * | 12/1992 | Solomon et al. | 204/404 |
| 5,186,798 A | * | 2/1993 | Sakai et al. | 204/400 |
| 5,316,633 A | * | 5/1994 | Sakai et al. | 204/404 |
| 5,719,911 A | * | 2/1998 | Hettiarachchi et al. | 204/404 |

OTHER PUBLICATIONS

Abstract presented at Swiss Association for Atomic Energy (SVA) Seminar on "Water Chemistry and Materials Behavior", Apr. 21–23, 1999, Brugg–Windisch, Switzerland, Experience of Duane Arnold With Noble Metal Chemical Addition, Robert L. Cowan.

Abstract presented at the VGB Chemistry Conference, Oct. 27, 1999, Essen, Germany, "Experience With Noble Metal Chemical Addition in BWRs", RL Cowan, S. Hettiarachchi, RJ Law, WD Miller and TP Diaz.

Tunold et al., Russ. J. Electrochem. 31, pp. 638–48, 1995, (CAS abstract only).*

* cited by examiner

*Primary Examiner*—Robert J. Warden, Sr.
*Assistant Examiner*—Kaj K. Olsen
(74) *Attorney, Agent, or Firm*—Robert P. Santandrea; Noreen C. Johnson

(57) ABSTRACT

A system and method for determining a noble metal concentration in a sample that is representative of a noble metal concentration in either a volume of water circulated through a nuclear reactor or a surface of a nuclear reactor component exposed to the volume of water. The system comprises: at least one standard having a predetermined concentration of the noble metal disposed its surface; an electrolyte bath for immersing one of the sample and the standard therein; an auxiliary electrode connectable to one of the sample and the standard; a power source connectable to a reference electrode and one of the standard and the sample; and a current measurement device capable of measuring a current passing between the auxiliary electrode and one of the sample and the standard. The power source is capable of providing a potential across the reference electrode and one of the sample and the standard, The noble metal concentration in the sample is determined relative to the predetermined concentration in the standard by comparing a sample current passing through the sample to a standard current passing through the standard.

43 Claims, 16 Drawing Sheets

SYSTEM AND METHOD FOR DETERMINING NOBLE METAL CONCENTRATIONS IN REACTOR COOLANT STREAMS

BACKGROUND OF THE INVENTION

The invention relates to the determination of noble metal concentrations in either a volume of water containing such noble metals or in components exposed to such water. More particularly, the present invention relates to a system and method for determining noble metal concentrations in either a volume of water or in components exposed to such water. Even more particularly, the invention relates to a system and method for determining the concentration of noble metals present in either nuclear reactor water during noble metal chemical addition to the water or in the surface of structural materials that have been exposed to the reactor water containing the noble metals.

Under the water chemistry conditions normally encountered during the operation of boiling water nuclear reactors (BWRs), strong oxidizing species, such as oxygen and hydrogen peroxide, are generated. The presence of such oxidizing species contribute to the intergranular stress corrosion cracking (IGSCC) of sensitized 304 stainless steel within the reactor. Naturally, IGSCC is known to be a major environment-related material performance problem within BWRs. It has been demonstrated that, by sufficiently lowering the concentrations of ionic impurities and oxidizing species in the reactor water, IGSCC can be mitigated. The electrochemical corrosion potential (ECP) of stainless steels and other active metals is known to be controlled mainly by the dissolved oxygen, hydrogen, and hydrogen peroxide concentrations in the BWR coolants and the hydrodynamic flow conditions within the coolant path. In order to evaluate or predict materials performance (including SCC as a function of time), it is extremely important to know the ECP value of the structural materials that are exposed to high temperature water within the reactor pressure vessel.

In hydrogen water chemistry (HWC), hydrogen is added to the feed water of a BWR to mitigate IGSCC. The primary purpose of the hydrogen addition is to reduce the concentrations of dissolved oxidants and thus lower the ECP to a value that is less than a critical value of −230 mV, measured against a standard hydrogen electrode (SHE), at which IGSCC susceptibility is markedly reduced. Hydrogen ($H_2$) levels in the feed water are always in the excess of the stoichiometric amount needed to react with either $O_2$ or $H_2O_2$ to form $H_2O$. However, several side effects of the HWC application, such as increased $N^{16}$ carry-over to the turbine and higher $Co^{60}$ deposition rates, have been reported. Also, the critical ECP value that is needed to prevent IGSCC is difficult to achieve in highly oxidizing and/or high water flow regimes.

Subsequent to the development of HWC, noble metal technology (NMT) was developed. By improving the catalytic properties of metal surfaces for the recombination of either hydrogen/oxygen or hydrogen peroxide/hydrogen to form water, NMT allows low ECP values to be achieved at much lower $H_2$ addition rates. This catalysis reduces the oxygen concentration at the metal surface to zero, thus causing the ECP to drop to its thermodynamic minimum (about≈−550 $mV_{SHE}$ in pure water at 288° C.). To achieve a stoichiometric excess of hydrogen, a H:O molar ratio of greater than 2:1, or a H:O weight ratio of greater than 1:8, is needed. This condition has been demonstrated to occur not only for pure noble metals and coatings, but also for very dilute noble metal alloys (NMA) or thermal spray coatings with powders of NMA. Recently, a technique for in-situ noble metal chemical addition (NMCA) on the oxide surfaces of various structural materials in high temperature water has been developed and applied to commercial BWRs in the United States, Europe, and Japan. Using NMCA, chemicals containing noble metals are injected directly into the reactor water and then are deposited onto the surfaces of reactor components that are exposed to the feed water. The surfaces of the reactor components are typically covered with an oxide outer layer. The noble metals are deposited onto the oxide layer, thus providing a catalytic site for both the $H_2/O_2$ and $H_2/H_2O_2$ recombination reactions. The ECP value needed to ensure protection of components from IGSCC can then be achieved through the addition of smaller amounts of hydrogen, thus avoiding many of the negative side effects that are frequently encountered at higher $H_2$ concentrations.

In order to control the loading levels of noble metals such as platinum (Pt) and rhodium (Rh), the NMCA application process that is currently used requires that the concentration of noble metals on both the surface of the reactor components and in the reactor water can be determined. In order to measure the noble metal concentration present on the surface of the reactor components both during and after the NMCA application, the oxide surfaces that have been treated with noble metals (such as Pt and Rh) are first immersed in aqua regia to dissolve the oxide layer containing the noble metals. A sample taken from the aqua regia solution is introduced into an inductively coupled plasma-mass spectrometer (ICP-MS) to determine the noble metal concentration. Because of the relatively long time required to dissolve the oxide layer containing the noble metals in aqua regia, about 3–4 hours are needed to obtain valuable information on the Pt and Rh concentrations by this analytical method. As the NMCA process normally takes about 48 hours to deposit the desired amount of noble metal on the surfaces of BWR components that are exposed to high temperature feed water, the ICP-MS method of analysis is unable to provide a timely determination of the noble metal concentration in either the feed water or the component surface.

In addition to the long period of time needed to dissolve the oxide layer containing the noble metals, the use of ICP-MS to determine the noble metal concentrations during the NMCA process has other disadvantages. One such disadvantage is the high cost of ICP-MS hardware. In addition to cost, an ICP mass spectrometer typically requires a dedicated lab environment, provides no in-situ analytical capability, and requires the use of hazardous reagents such as aqua regia solutions. Furthermore, the sharing of ICP-MS resources by multiple users is precluded by scheduling concerns. All commercial BWRs are treated using the NMCA process during reactor shutdowns and most follow a common regular shutdown schedule. Thus, ICP-MS instruments are in high demand during the periods when such shutdowns take place.

The ICP-MS method of determining the noble metal concentration in BWR feed water and on component surfaces is slow, costly, and logistically awkward. Therefore, what is needed is a cost-effective system for determining the concentration of noble metals in the feed water of a BWR and BWR components that are exposed to the feed water. What is also needed is a timely, cost-effective method for analyzing the noble metal concentration in the feed water of a BWR. Finally, what is also needed is a timely, cost-effective method of determining the noble metal concentration in surfaces of BWR components exposed to feed water containing noble metals in solution.

BRIEF SUMMARY OF THE INVENTION

The present invention meets these and other needs by providing a new system and method for detecting and quantifying the amount of noble metals, such as platinum and rhodium, either dissolved in a volume of water or deposited onto a solid that has been exposed to the volume of water. More particularly, the present invention provides a system and method for determining the noble metal concentration in either the reactor water or the surface of reactor materials that have been exposed to reactor water containing noble metals. The system and method are capable of determining noble metal concentrations during periods of noble metal addition or during plant operation following such addition.

Accordingly, one aspect of the present invention is to provide a system for determining a noble metal concentration in a collection sample, the collection sample having a surface and at least one noble metal disposed thereon. The noble metal concentration in the collection sample is representative of a first concentration of the noble metal in one of a volume of water and a surface of a solid component exposed to the volume of water. The system comprises: at least one standard having a standard surface and a predetermined concentration of the noble metal disposed thereon; an electrolyte bath for immersing one of the collection sample and the standard therein; an auxiliary electrode electrically connectable to one of the collection sample and the standard and being immersible in the electrolyte bath; and a power source electrically connectable to a reference electrode and one of the standard and the collection sample, the reference electrode being immersible in the electrolyte bath; wherein the power source is capable of providing a potential across the reference electrode and one of the collection sample and the standard, and a current measurement device capable of measuring a current passing between the auxiliary electrode and one of the collection ample and the standard. The noble metal concentration in the collection sample is determined relative to the predetermined concentration in the standard by comparing a ample current passing through the collection sample to a standard current passing through the standard.

A second aspect of the invention is to provide a cyclic voltametric apparatus for measuring a current produced by formation of one of hydrogen and oxygen in the presence of at least one noble metal. The cyclic voltametric apparatus comprises: an electrode having a surface and the noble metal disposed thereon, an auxiliary electrode electrically connectable to the electrode and a reference electrode, each of the electrode, the auxiliary electrode, and the reference electrode being immersible in an electrolyte bath; a power source electrically connectable to each of the electrode and the reference electrode, the power source being capable of providing a potential between the reference electrode and the electrode and cyclically varying the potential between at least two predetermined potentials relative to the reference electrode; and a current measurement device capable of measuring a current passing between the electrode and the auxiliary electrode. The hydrogen current produced by formation of hydrogen and an oxygen current produced by formation of oxygen are measured by the current measurement device during at least one reversibly cyclic application of the potential between a first potential at which hydrogen forms and a second potential at which oxygen forms.

A third aspect of the invention is to provide a system for determining a noble metal concentration in a collection sample, the collection sample having a surface and at least one noble metal disposed thereon. The noble metal concentration in the collection sample is representative of a first concentration of the noble metal in one of a volume of water in a boiling water nuclear reactor and a surface of a solid component in the boiling water nuclear reactor that is exposed to the volume of water. The system comprises: at least one standard having a standard surface and a predetermined concentration of the noble metal disposed thereon; an electrolyte bath for immersing one of the collection sample and the standard therein, the electrolyte bath comprising an inorganic acid; an auxiliary electrode, the auxiliary electrode being electrically connectable to one of the collection sample and the standard, and a reference electrode, each of the auxiliary electrode and the reference electrode being immersible in the electrolyte bath; a power source electrically connectable to the reference electrode and one of the collection sample and the standard, the power source being capable of providing a potential between the reference electrode and one of the collection sample and the standard and cyclically varying the potential between at least two predetermined potentials relative to the reference electrode; and a current measurement device capable of measuring a current passing between the auxiliary electrode and one of the collection sample and the standard. A hydrogen current produced by formation of hydrogen in the electrolyte bath and an oxygen current produced by formation of oxygen in the electrolyte bath are measured by the current measurement device during at least one reversibly cyclic variation of the potential between a first potential at which hydrogen forms and a second potential at which oxygen forms. The noble metal concentration in the collection sample is determined relative to the predetermined concentration by comparing a collection sample hydrogen current and a collection sample oxygen current measured for the collection sample to a standard hydrogen current and a standard oxygen current measured for the standard.

A fourth aspect of the present invention is to provide a method for determining a noble metal concentration in a collection sample, the collection sample containing at least one noble metal in a concentration that is representative of a noble metal concentration in one of a volume of water and a surface of a solid component exposed to the volume of water. The method comprises the steps of: immersing the collection sample into an electrolyte solution; connecting the collection sample to an auxiliary electrode; connecting the collection sample and a reference electrode to a power source; applying a potential between the collection sample and the reference electrode; measuring a current passing between the collection sample and the auxiliary electrode; providing at least one standard having a predetermined concentration of the noble metal; immersing the standard into a second electrolyte solution; connecting the collection sample to an auxiliary electrode; connecting the standard and a reference electrode to a power source; applying a potential between the standard and the reference electrode; measuring a current passing between the standard and the auxiliary electrode; and comparing the current passing through the collection sample to the current passing through the standard, thereby determining the concentration of noble metal present in the collection sample relative to the predetermined concentration of noble metal present in the standard.

Finally, a fifth aspect of the present invention is to provide a method of determining a noble metal concentration in a collection sample that is representative of a noble metal concentration in one of a volume of water circulated through a nuclear reactor and a surface of a nuclear reactor component exposed to the volume of water. The method comprises the steps of: providing at least one collection sample; exposing the collection sample to the volume of water; immersing the collection sample into an electrolyte solution; connecting the collection sample to an auxiliary electrode; connecting the collection sample and a reference electrode to a power source; applying a potential between the collection sample and the reference electrode; measuring a current passing between the collection sample and the auxiliary electrode; providing at least one standard having a predetermined concentration of the noble metal; immersing the standard into a second electrolyte solution; connecting the standard to an auxiliary electrode; connecting the standard and a reference electrode to a power source; applying a potential between the standard and the reference electrode; measuring a current passing between the standard and the auxiliary electrode; and comparing the current passing through the collection sample to the current passing through the standard, thereby determining the concentration of noble metal present in the collection sample relative to the predetermined concentration of noble metal present in the standard.

These and other aspects, advantages, and salient features of the invention will become apparent from the following detailed description, the accompanying drawings, and the appended claims.

DETAILED DESCRIPTION OF THE INVENTION

Figure 1:
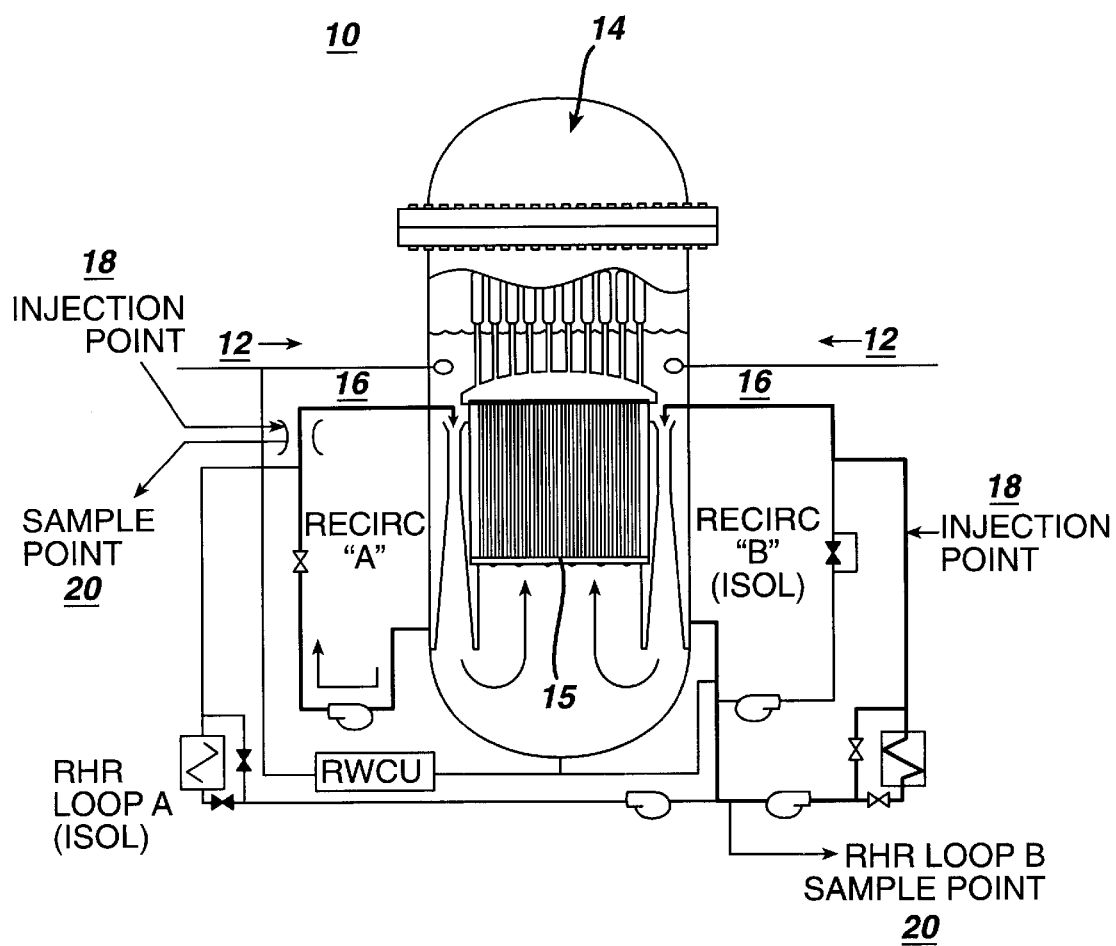
FIG. 1 is a schematic diagram of a BWR reactor showing the locations of injection points, where noble metals are introduced into the reactor feed water, and sampling points, where samples are taken for noble metal analysis.

In the following description, like reference characters designate like or corresponding parts throughout the several views shown in the figures. It is also understood that terms such as "top," "bottom," "outward," "inward," and the like are words of convenience and are not to be construed as limiting terms.

Referring to the drawings in general and to FIG. 1 in particular, it will be understood that the illustrations are for the purpose of describing a preferred embodiment of the invention and are not intended to limit the invention thereto.

FIG. 1 is a schematic diagram of a BWR nuclear reactor 10, having a pressure vessel 14, which contains the reactor core 15. Feed water is introduced into the pressure vessel 14 through feed water lines 12, where it is heated by the core 15. Heated water is then pumped out of the pressure vessel 14 through recirculation lines 16.

Many of the reactor components located within the pressure vessel 14 are formed from stainless steel. As previously mentioned, such components are susceptible to intergranular stress corrosion cracking (ISCC). Noble metal chemical addition (NMCA) mitigates ISCC of such components by depositing noble metals in-situ on the oxide surface of such structural materials. The use of the NMCA technique in BWRs is described, for example, in the paper "Experience of Duane Arnold with Noble Metal chemical Addition," presented by Robert L. Cowan at the Swiss Association for Atomic Energy Seminar on Water Chemistry and Materials Behavior," Apr. 21–23, 1999, in Brugg-Windisch, Switzerland. Compounds containing noble metals are injected at injection points 18 into recirculation lines 16 and carried into the pressure vessel 14. Samples are withdrawn for analysis through sampling points 20, located in the recirculaltion lines 16.

Figure 2:
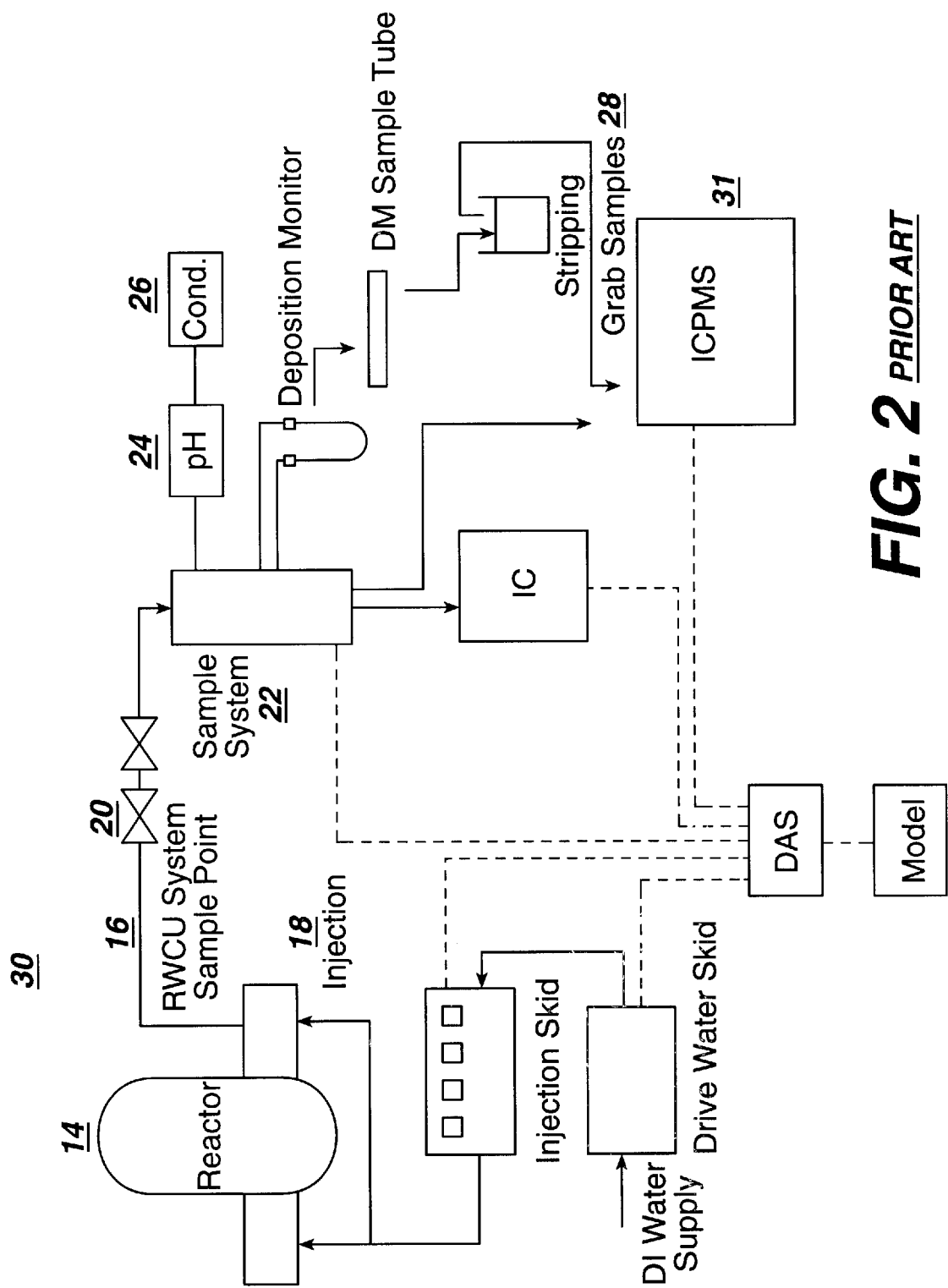
FIG. 2 is a schematic diagram of a prior-art system for analysis of noble metal concentrations in BWR components and feed water.

A prior-art system 30 for determining the noble metal concentration in the high temperature water and components exposed to such water in a BWR 10 is schematically shown in FIG. 2. The prior-art system 30 provides for obtaining liquid "grab samples" as well as samples of metal tubing that have been exposed to the feed water containing noble metals at sample point 22. Analysis for noble metals in the samples is performed using an inductively coupled mass spectrometer (ICP-MS) 31.

In contrast to the prior-art approach to determining the noble metal concentration by ICP-MS, the present invention is based upon electrochemical techniques that can be used to characterize species that are present in component surfaces or in solution and quantitatively measure the concentrations of the noble metals of interest. These electrochemical methods include CV (cyclic voltametry), LSV (linear sweep voltametry), ASV (anodic stripping voltametry), DPA (differential pulse amperometry), and SWV (square wave voltametry). These illustrative techniques provide information about the electroactivity of the electrode or the solution species by measuring both the current and potential of the species. Cyclic voltametry, for example, measures the current during a potential sweep. The resulting peak current and potential are directly related to the quantity and identification of either a surface or solution species, respectively. This particular embodiment of the present invention focuses on analyzing the noble metal concentration that are deposited on the metal or metal oxide surface during the NMCA process application by CV.

It is well known that $H_2$ evolution catalytically occurs at noble metals such as Pt and Rh with very little over-potential according to the general reaction, $$2H^+ + 2e^- \rightarrow H_2 \tag{equation 1}$$

while the $H_2$ evolution at other metal surfaces such as stainless-steel, mercury, and iron occurs with very large over-potential. Thus, the rate of $H_2$ evolution—i.e., the rate at which $H^+$ is reduced at the noble metal—is proportional to the surface concentration of the noble metal, such as Pt, Rh, and combinations thereof. Therefore, the surface concentration of Pt or Rh at the surface of metallic components or samples in the BWR during the NMCA application process can be directly determined by measuring the cathodic—or reduction—current for $H_2$ evolution in the presence of the sample.

Figure 5:
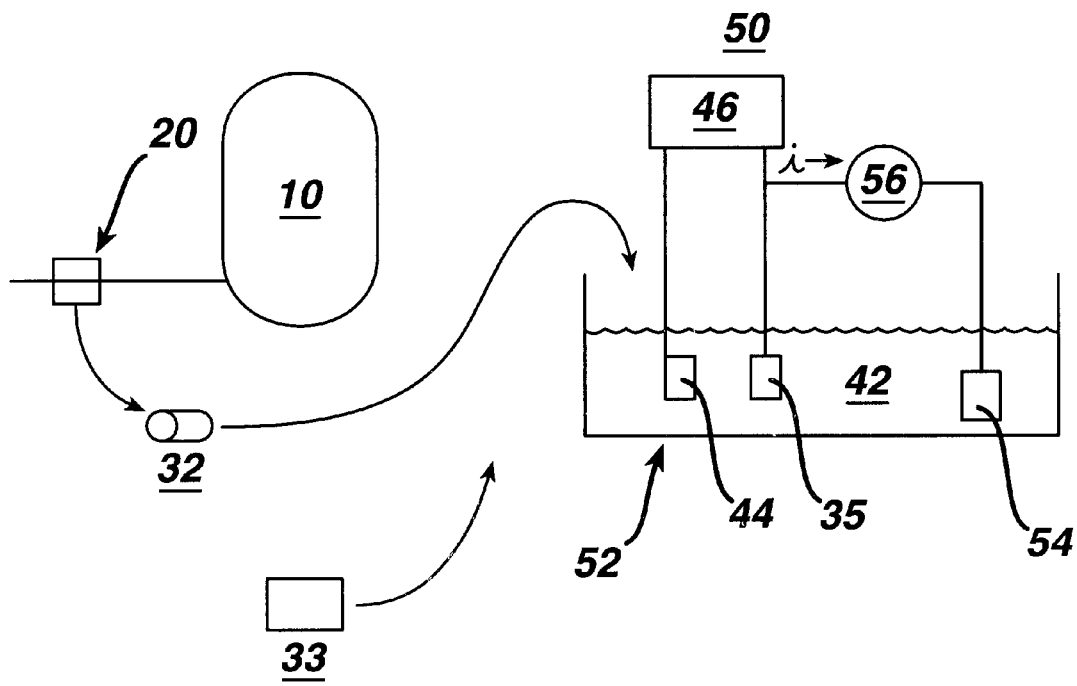
FIG. 5 is a schematic diagram showing the system of the present invention.

The system 50 of the present invention for determining noble metal concentrations in either high temperature water circulating through a BWR or in BWR components that are exposed to such water is shown in FIG. 5. Once exposed at the sampling point 20 to the high temperature water containing at least one noble metal, such as platinum or rhodium, a collection sample 32 is removed from the sampling point 20 in the BWR reactor 10. The form and composition of the collection sample 32 depends on whether the noble metal concentration in the feed water or the in the reactor components is to be determined. To analyze the noble metal concentration in the feed water, for example, a carbon electrode 33, appropriately sized for placement in a recirculation line 16 of the BWR reactor 10, is preferred.

Figure 3:
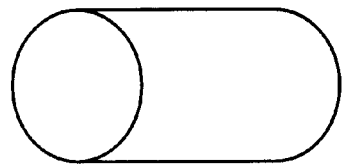
FIG. 3 is a perspective view of a stainless steel collection sample of the Preferred Embodiment.
Figure 4:
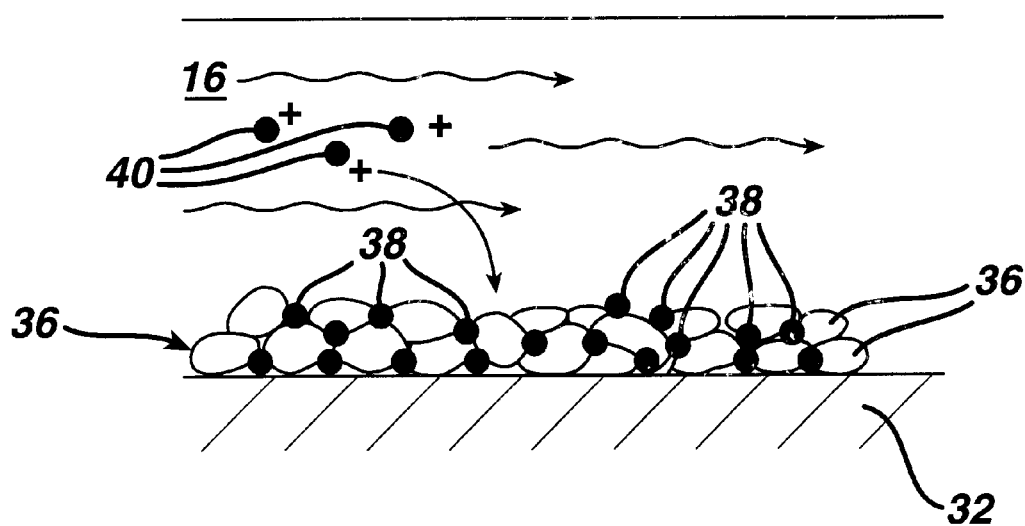
FIG. 4 is a cross-sectional schematic view of a surface of a collection sample being exposed to BWR water containing a noble metal.

When the noble metal concentration in BWR components is to be determined, a collection sample 32 comprising a metallic specimen is used. The metallic specimen is formed from materials such as carbon steel, low-alloy steel, stainless steel, nickel-base alloys, and the like. Although the collection sample 32 is preferably a segment of stainless steel tubing, as shown in FIG. 3, the collection sample 32 may be shaped into other forms, such as a rod, plate, coupon, and the like. Multiple collection samples 32 can be provided and located at sample points 20 within the recirculation loop 16. As shown in FIG. 4, the surface of the collection sample 32, like BWR components having a composition similar thereto, develops a thin layer of metal oxide 36 when exposed to the BWR feed water. During the NMCA process, at least one noble metal 38 is deposited in elemental form into the metal oxide layer 36, as well as on the surface of the metal oxide layer 36.

Following exposure to the feed water, the collection sample 32 is removed from the sample point 20 and immersed in an electrolyte bath 52. The electrolyte bath 52 is preferably a weak inorganic acid, such as sulfuric acid or nitric acid. Neutral and basic electrolytes can also be employed, however, to yield similar results.

The collection sample 32 is then electrically connected to a power source 46 and used as an electrode 35. A reference electrode 44 is connected to the power source 46 and inserted in the electrolyte bath 52. An auxiliary electrode 54 is connected to the collection sample 32 and inserted in the electrolyte bath. A potential between the collection sample 32, serving as electrode 35, and the reference electrode 44 is then applied by the power source 46. The current passing between the auxiliary electrode 54 and the collection sample 32, serving as electrode 35, is measured by a current measurement device 56, such as an ammeter or the like.

Any available reference electrode, such as a Ag|AgCl electrode, a Hg|HgO electrode, a saturated calomel electrode, a platinum electrode, and the like, can be used as the reference electrode 44. The auxiliary electrode 54 is preferably a carbon electrode.

The power source 46 is preferably a potentiostat that allows the potential between the collection sample and the reference electrode to be varied.

Figure 6:
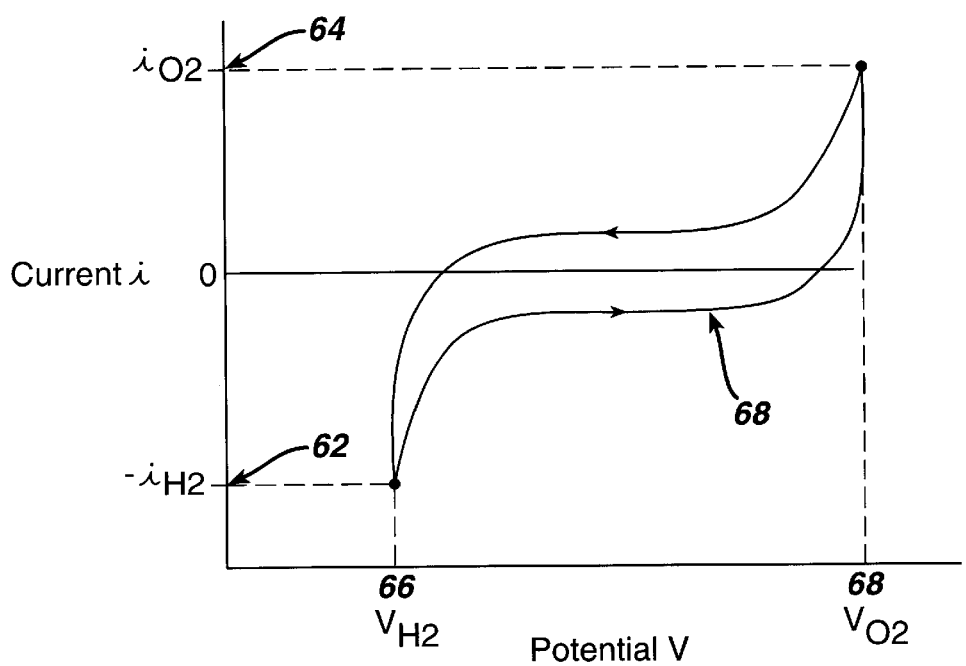
FIG. 6 is a cyclic voltametry plot of current vs. potential.

FIG. 6 is a representative cyclic voltametry (CV) plot of electrode current vs. potential obtained according to the present invention. A first potential 66 between the collection sample 32, serving as electrode 35, and the reference electrode 44 is applied by the power source 46. The first potential 66, shown in FIG. 6, is the reduction potential for the reduction of $H^+$ according to equation 1. The hydrogen evolution current $I(H_2)$62, which is produced by the reduction of $H^+$ according to equation 1 on the noble metal 38 that is present in the metal oxide layer 36, passes between the collection sample 32 and auxiliary electrode 54 and is measured at the first potential 66 by the current measurement device 56. The potential between the collection sample 32 and the reference electrode 44 is then cycled—i.e., "swept"—from the potential for the hydrogen reduction reaction 62 to a second potential 68, which is the potential for the reaction which generates oxygen:

$$2H_2O \rightarrow O_2 + 4H^+ + 4e^- \tag{equation 2}$$

The cycling of the potential between the collection sample 32 and reference electrode 54 is reversible; i.e., the potential can be cycled in the opposite direction from the second potential 68 to the first potential 66. The oxygen evolution current $I(O_2)$64, which is produced by the generation of $O_2$ according to equation 2 on the noble metal 38 that is present in the metal oxide layer 36, passes between the collection sample 32 and auxiliary electrode 54 and is measured at the second potential 68 by the current measurement device 56. The $H_2$ evolution current 62 and $O_2$ evolution current 64 measured for the collection sample solution 32 are used to calculate a ratio $i(H_2)/i(O_2)$ of the evolution currents for the collection sample solution 32.

The noble metal concentration present in the metal oxide layer 36 of the collection sample 32 is then determined by comparing the ratio of the $H_2$ and $O_2$ evolution currents measured for the collection sample 32 to the ratio of the $H_2$ and $O_2$ evolution currents that have been determined for at least one standard 33 formed from the same material as the collection sample 32 and having a known amount of the noble metal 38 deposited upon its surface. Cyclic voltametry measurements in which the standard 33, rather than the collection sample 32, is used as the electrode 35 are performed on the standard 33. Essentially the same conditions and procedures as those used in the CV measurements carried out on the collection sample 32 are employed in the CV measurements that are performed on the standard 33. A value for the $i(H_2)/i(O_2)$ ratio of the evolution currents obtained for the standard 33 is calculated from the CV results. The $i(H_2)/i(O_2)$ ratio obtained for the collection sample 32 can be divided by the value of the $i(H_2)/i(O_2)$ ratio obtained for the standard 33:

$$[i(H_2)/i(O_2)]_{sample}/[i(H_2)/i(O_2)]_{standard} = \text{concentration fraction of sample} \tag{3}$$

to yield a noble metal concentration fraction (i.e., the noble metal concentration of the collection sample 32 relative to the noble metal concentration of the standard 33) for the collection sample 32.

Figure 7:
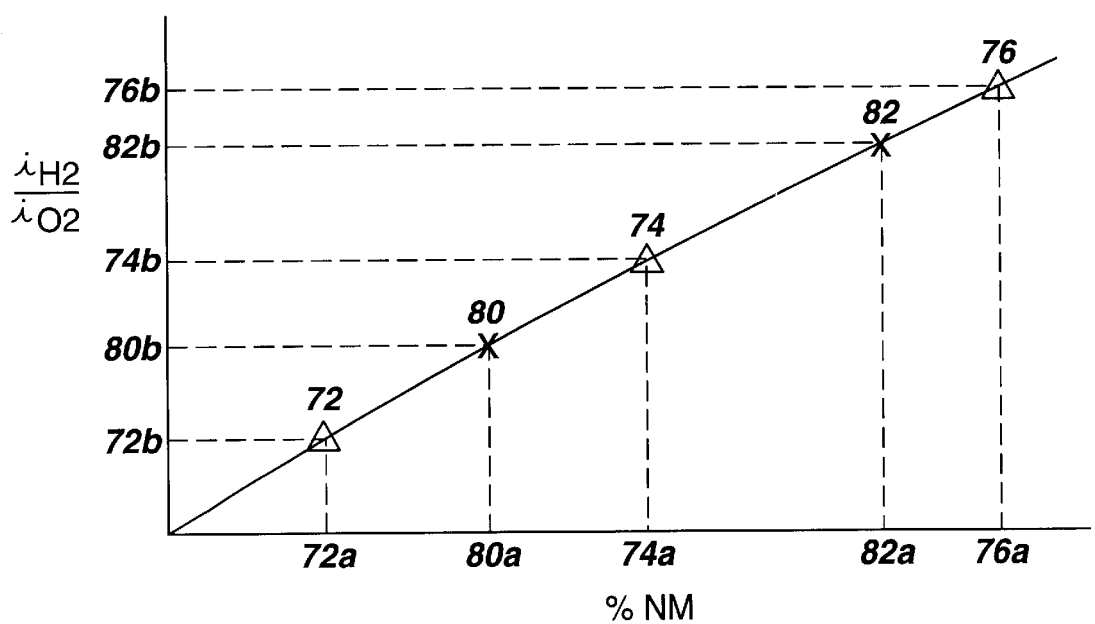
FIG. 7 is a plot of noble metal concentration vs. the ratio of $H_2$ evolution current to $O_2$ evolution current.
Figure 8:
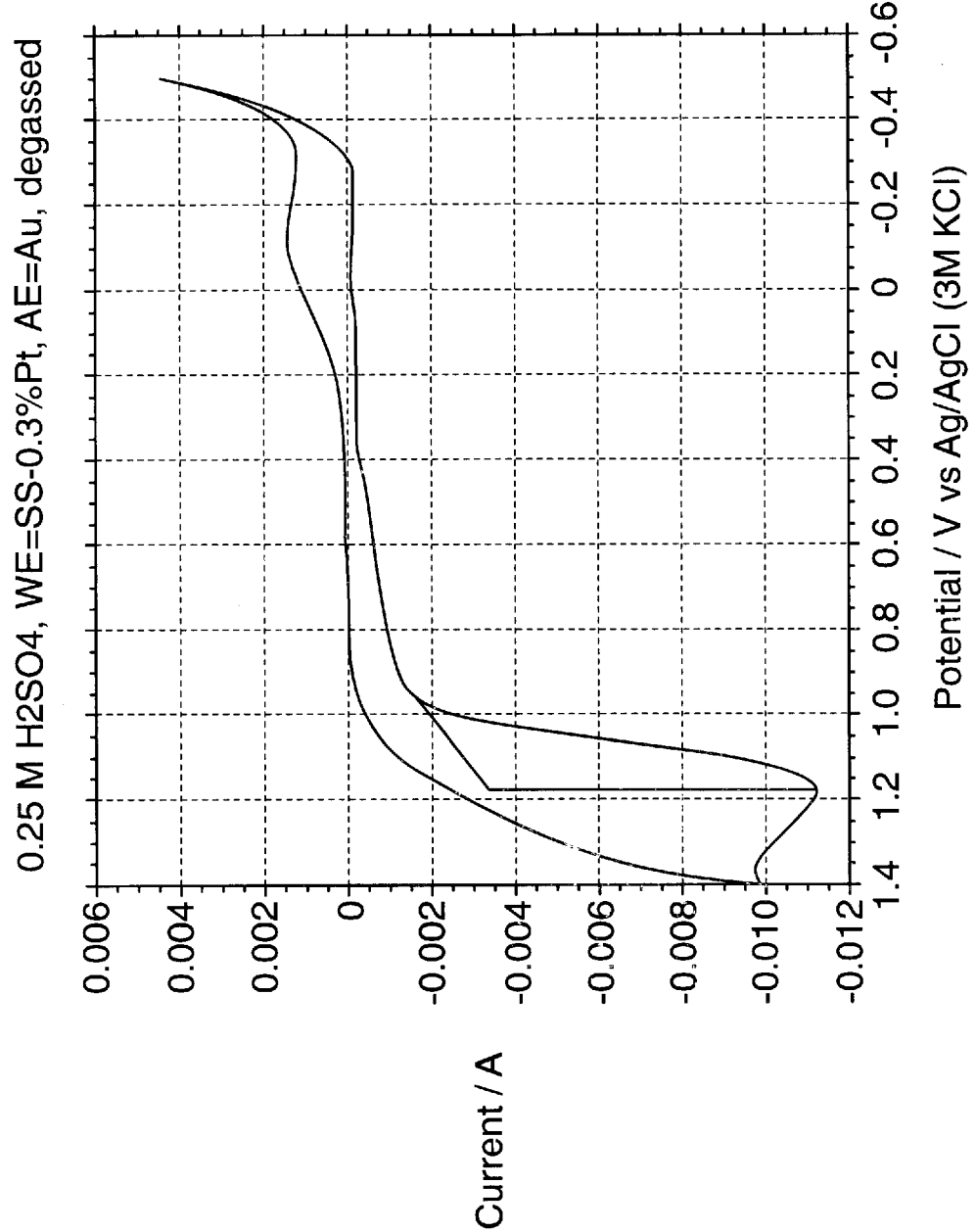
FIG. 8 is a plot of cyclic voltametry (CV) behavior of 316 SS+0.3% Pt in 0.25M $H_2SO_4$ at 25° C.
Figure 9:
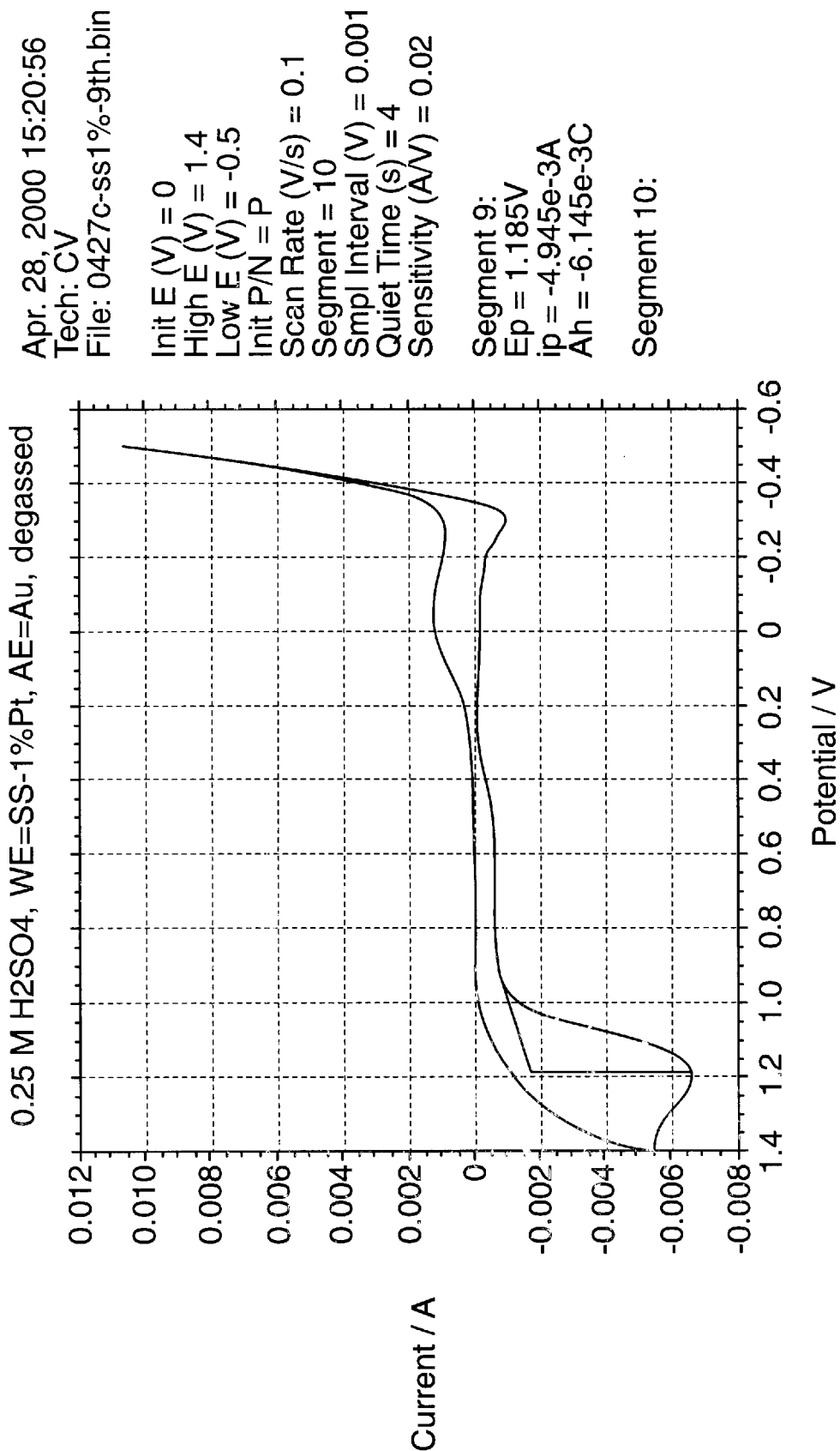
FIG. 9 is a plot of CV behavior of 316 SS+1% Pt in 0.25M $H_2SO_4$ at 25° C.
Figure 10:
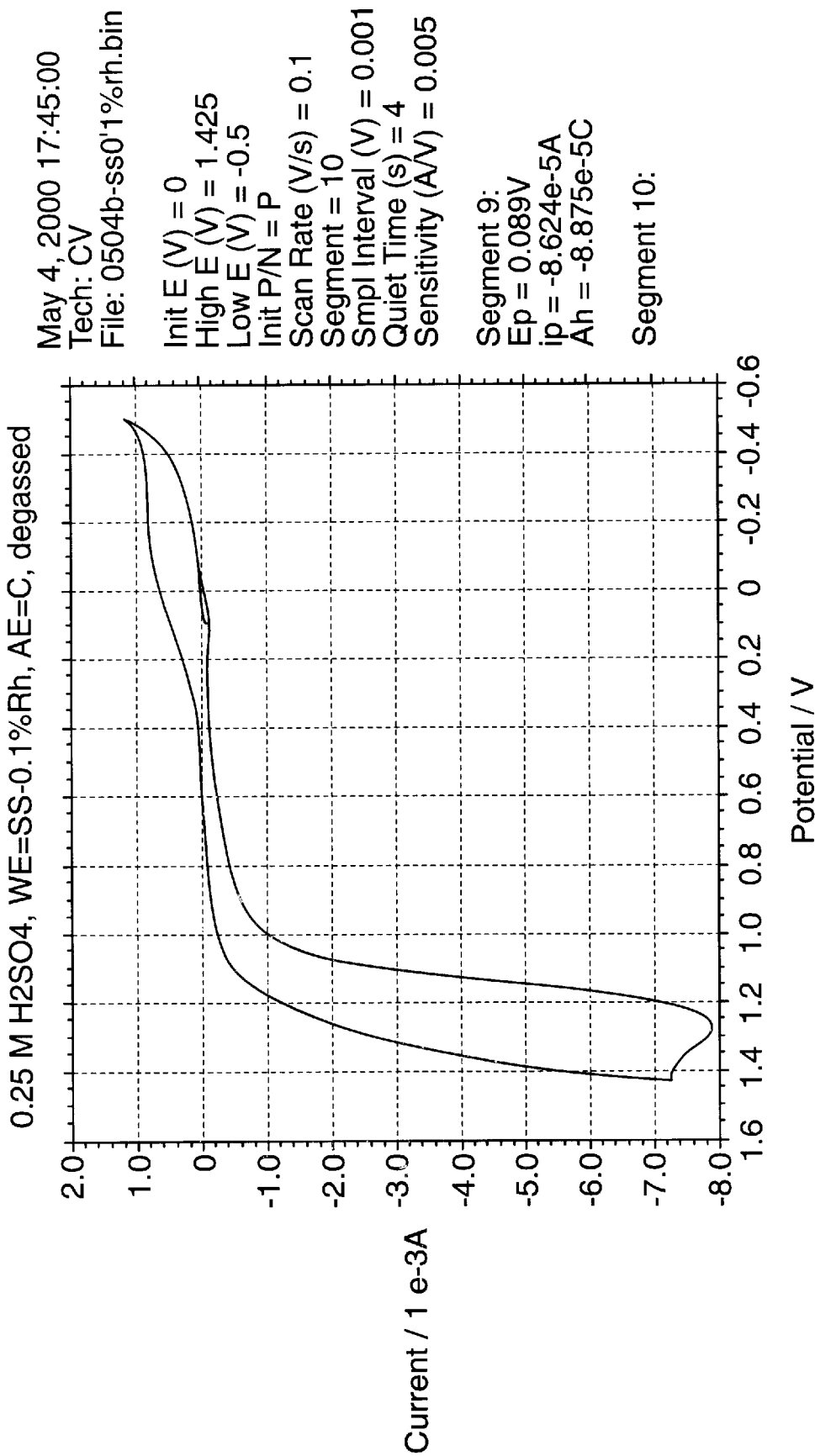
FIG. 10 is a plot of CV behavior of 316 SS+0.1% Rh in 0.25M $H_2SO_4$ at 25° C.
Figure 11:
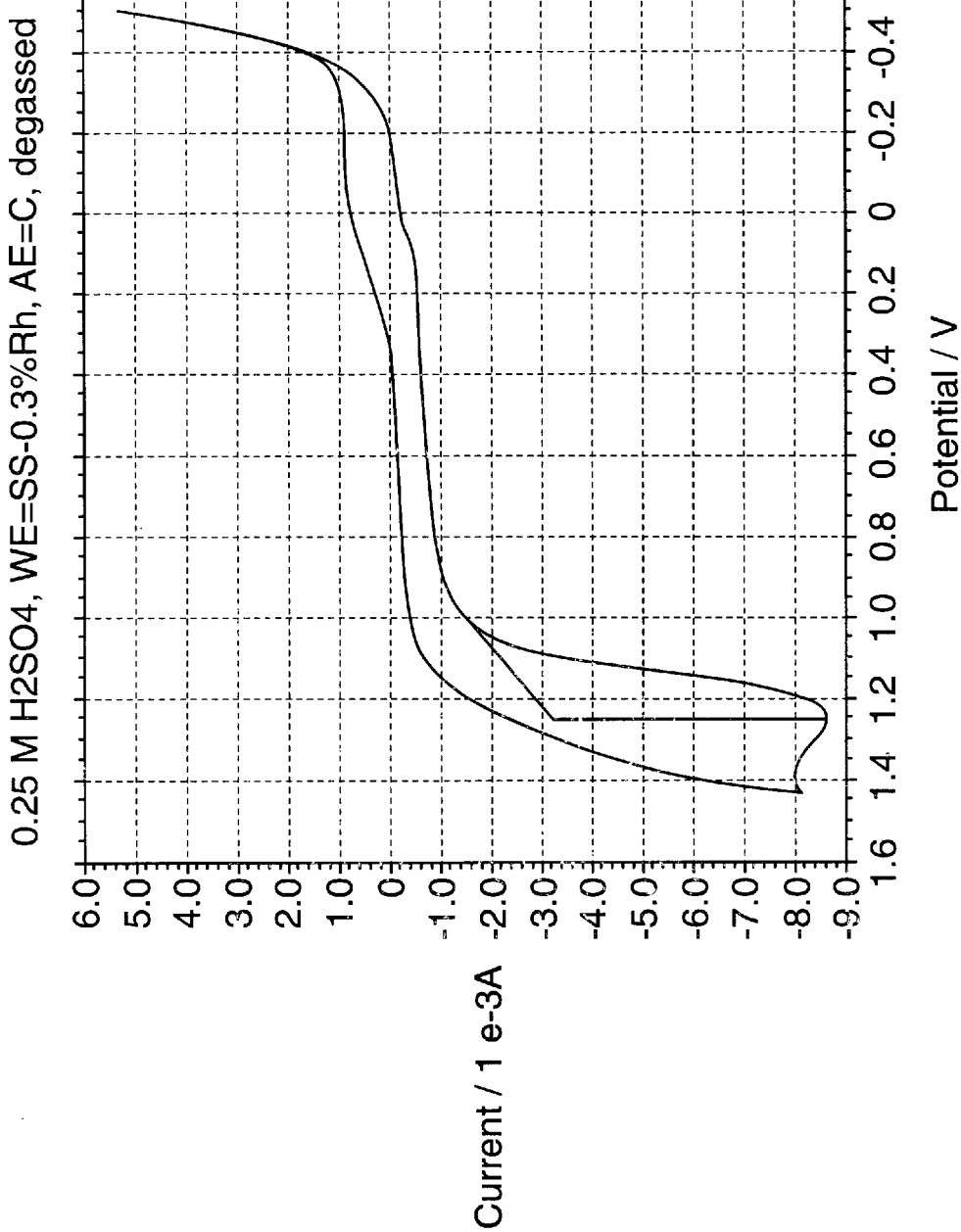
FIG. 11 is a plot of CV behavior of 316 SS+0.3% Rh in 0.25M $H_2SO_4$ at 25° C.
Figure 12:
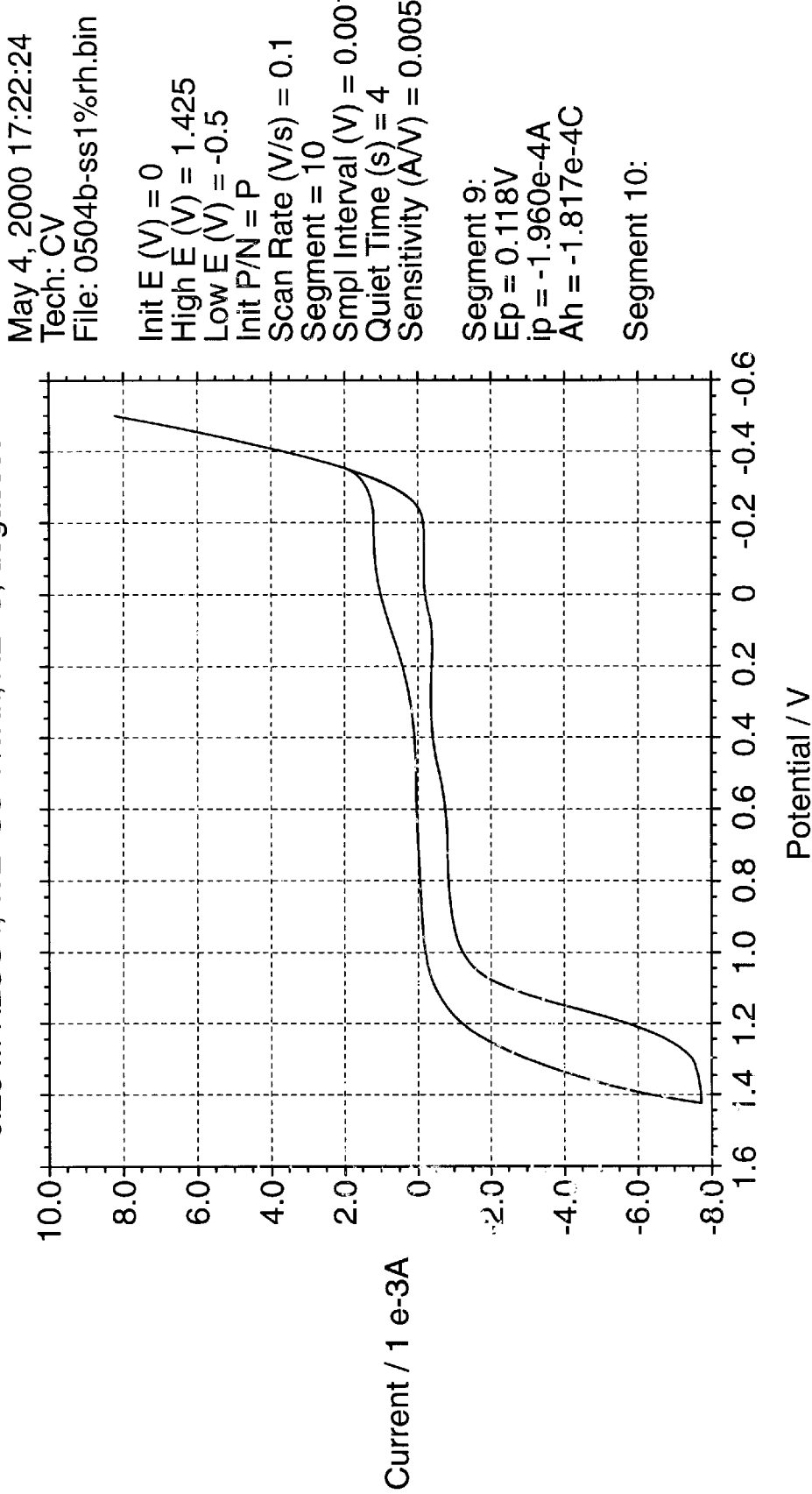
FIG. 12 is a plot of CV behavior of 316 SS+1% Rh in 0.25M $H_2SO_4$ at 25° C.

Preferably, a series of standards 72, 74, 76, each having a different known noble metal concentration 72a, 74a, 76a, respectively, are prepared. Cyclic voltametry measurements are performed on the standards 72, 74, 76 and $i(H_2)/i(O_2)$ values obtained for each standard. The respective $i(H_2)/i(O_2)$ values 72b, 74b, 76b, obtained for each standard are then plotted as a function of the known noble metal concentrations 72a, 74a, 76a of the standards 72, 74, 76. FIG. 7 is representative of such a plot, in which standard solutions 72, 74, and 76, having noble metal concentrations 72a, 74a, and 76a, and $i(H_2)/i(O_2)$ values 72b, 74b, and 76b, respectively, are shown. The $i(H_2)/i(O_2)$ values of the standards 72, 74, 76 vary linearly as a function of their respective noble metal concentrations. Similarly, CV measurements are carried out on collection samples 80 and 82. Having determined the respective $i(H_2)/i(O_2)$ ratios 80b and 82b from CV measurements for collection samples 80 and 82, the respective noble metal concentrations 80a and 82a of these collection samples can then be determined from the plot shown in FIG. 7.

The system and method of the present invention for determining the noble metal concentration in either the feed water or components exposed to the feed water provides a quick, cost-effective alternative to the analytical systems and methods currently employed. Analysis time is reduced from 2–4 hours to 10–20 minutes, thereby providing timely information on noble metal concentrations both during and after the NMCA.

The features of the present invention are illustrated by the following example.

EXAMPLE

Figure 13:
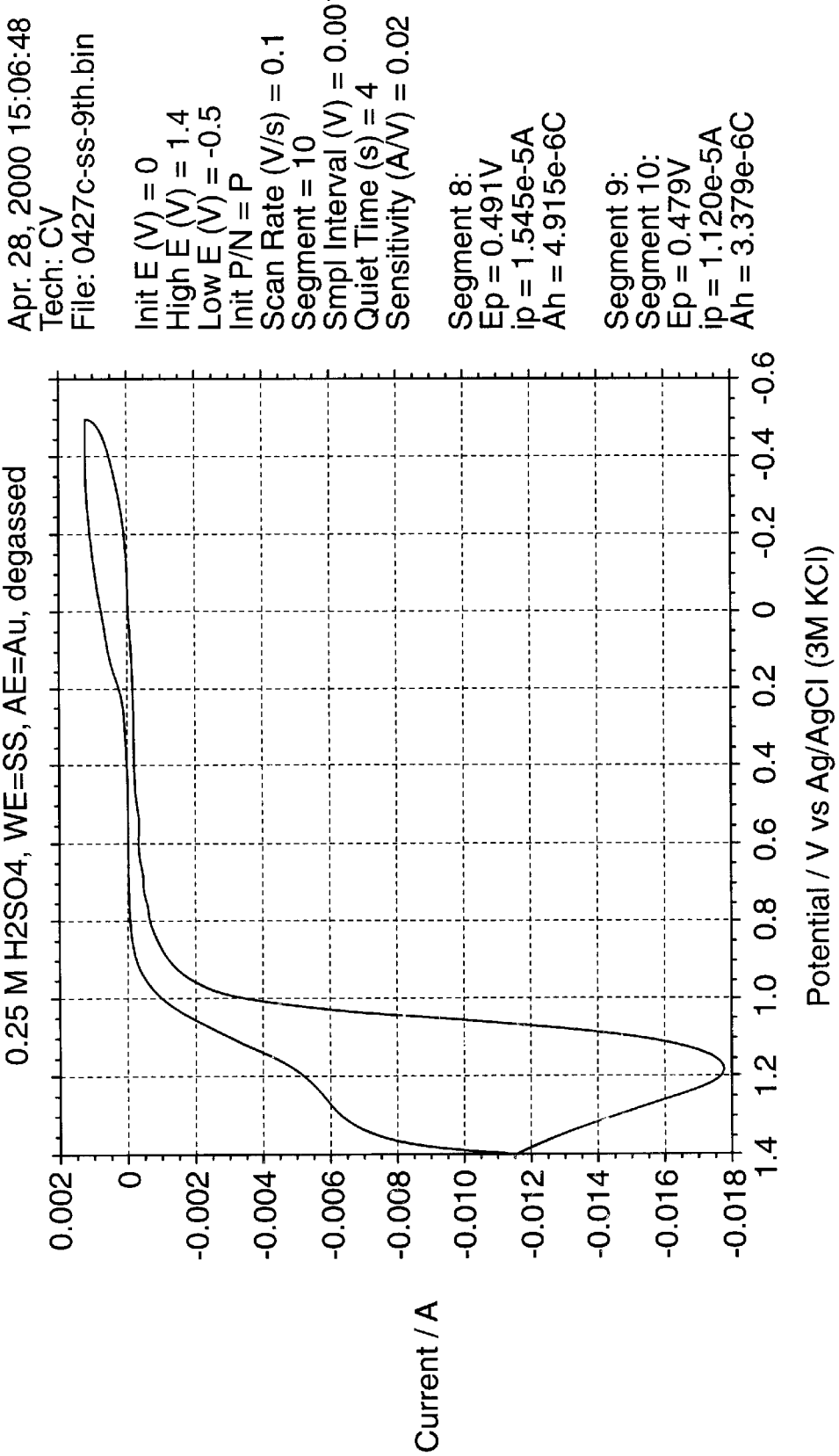
FIG. 13 is a plot of CV behavior of 316 SS in 0.25M $H_2SO_4$ at 25° C.
Figure 14:
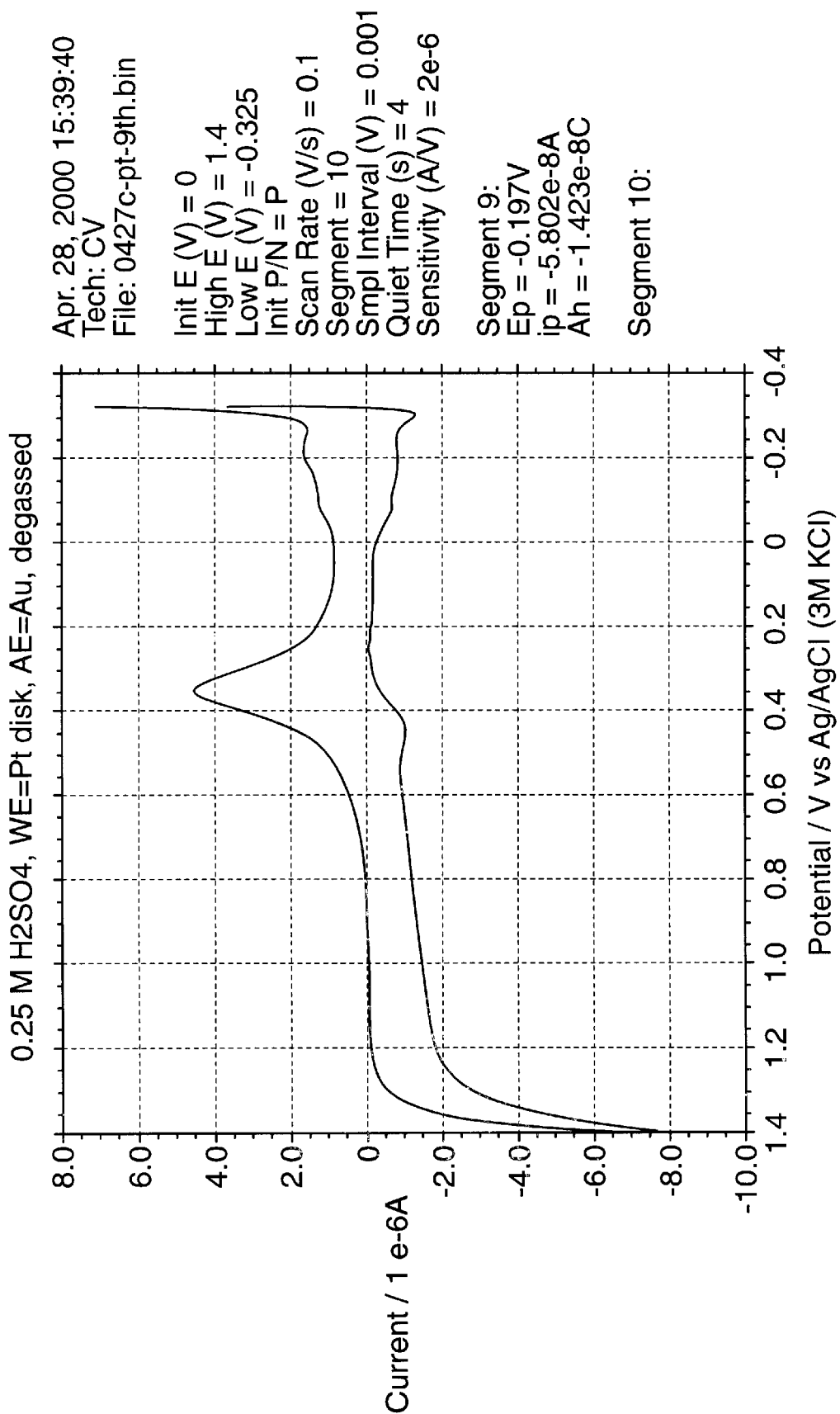
FIG. 14 is a plot of CV behavior of pure Pt in 0.25M $H_2SO_4$ at 25° C.
Figure 15:
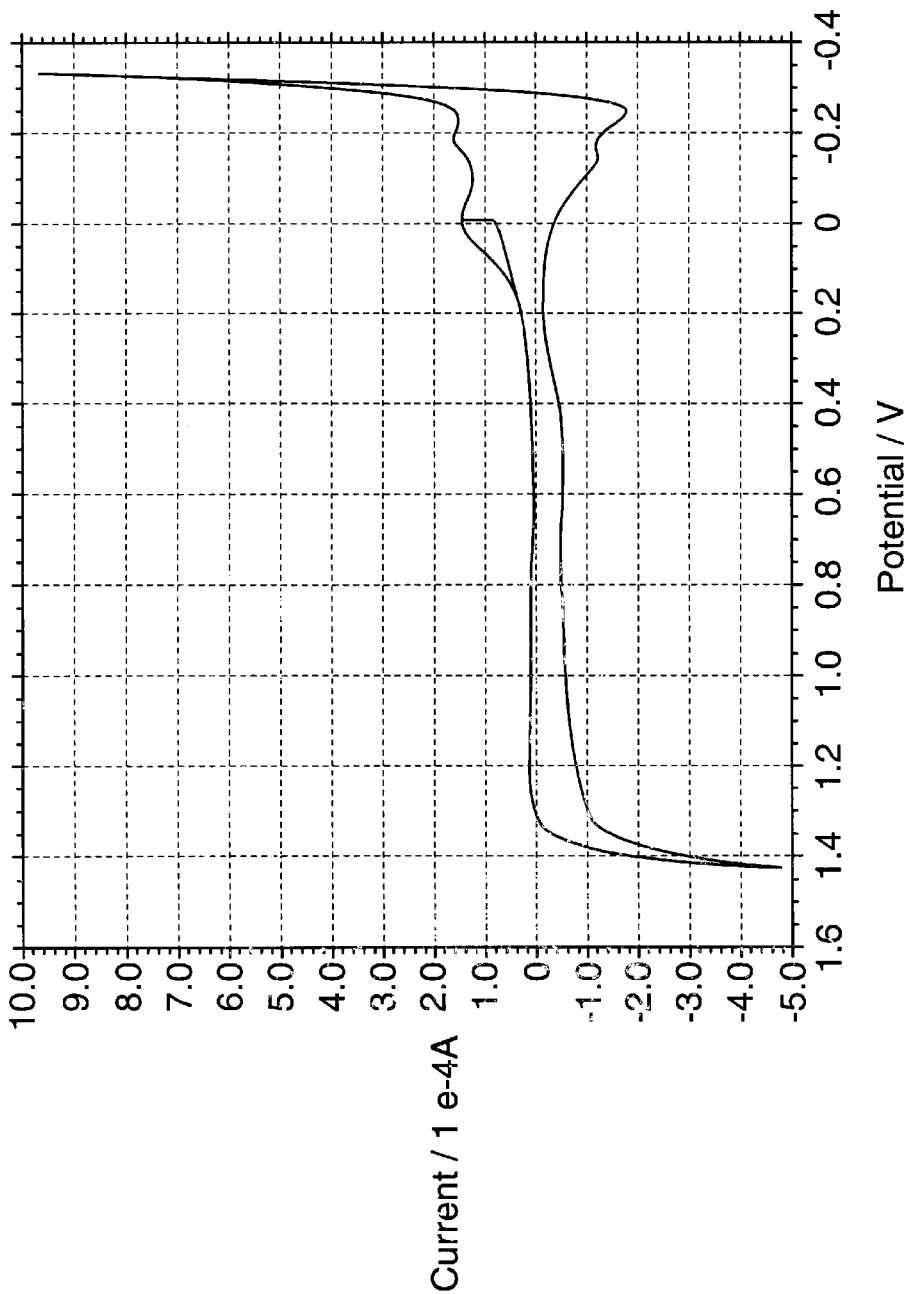
FIG. 15 is a plot of CV behavior of pure Rh in 0.25M $H_2SO_4$ at 25° C.

Samples of 316 stainless steel containing various amounts of platinum (0.3 wt % Pt, and 1.0 wt % Pt) and rhodium (0.1 wt % Rh, 0.3 wt % Rh, and 1.0 wt % Rh) were tested in 0.25M $H_2SO_4$ solution at 25° C. Cyclic voltametry data for these samples are presented in FIGS. 8–12, and CV data obtained on Type 316 SS, pure Pt, and pure Rh are shown in FIGS. 13—15, respectively. Other electrolytes such as different concentration (0.05–2 M) of $H_2SO_4$ have also been tested and the results revealed that they can also be used. Neutral and basic electrolytes can also be employed to provide similar results.

Figure 16:
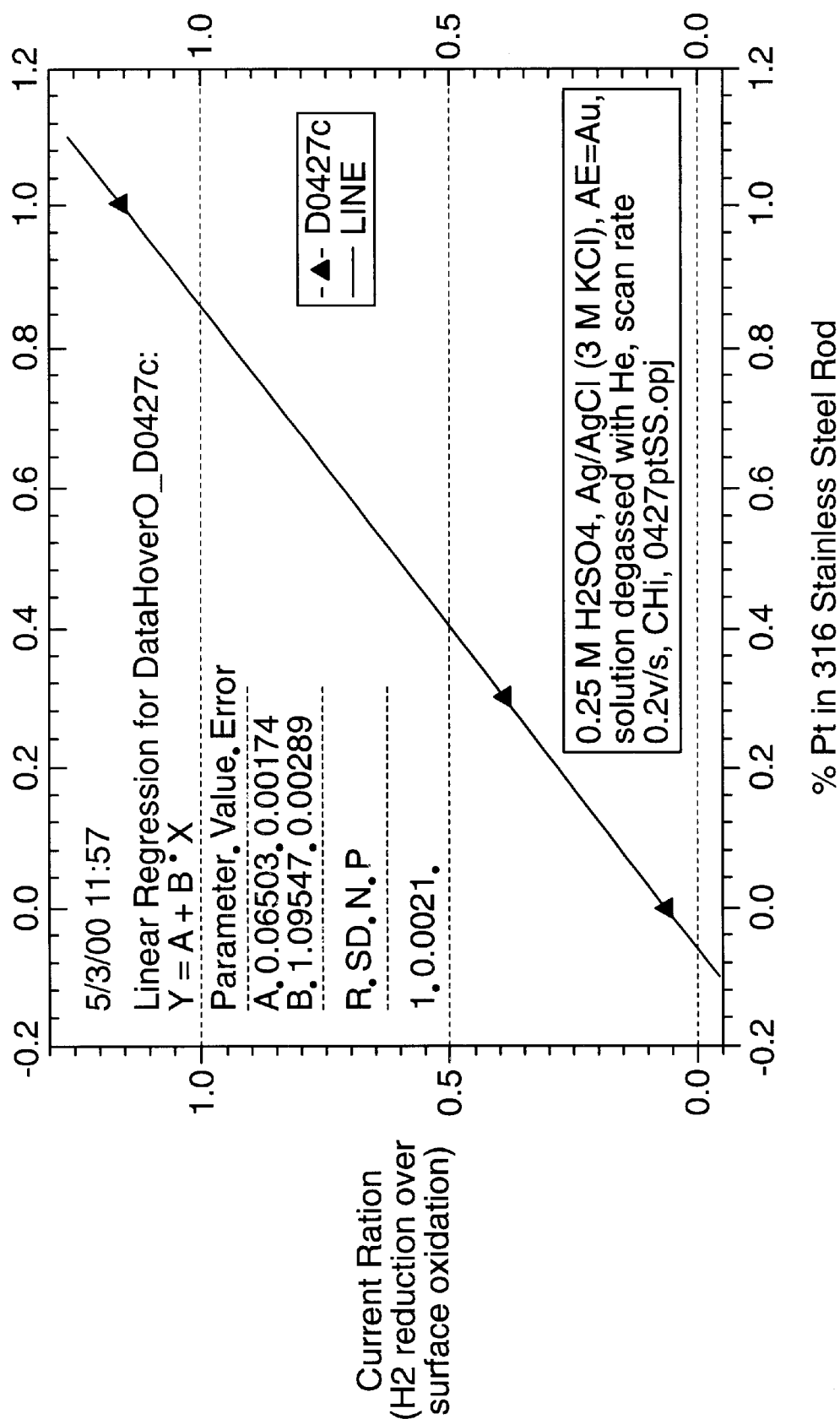
FIG. 16 is a plot of the relationship between Pt concentration and current ratio of reduction (at −0.5V vs a Ag|AgCl reference electrode) to oxidation (about 1.2V vs a Ag|Ag reference electrode) in 0.25M $H_2SO_4$ at 25° C.
Figure 17:
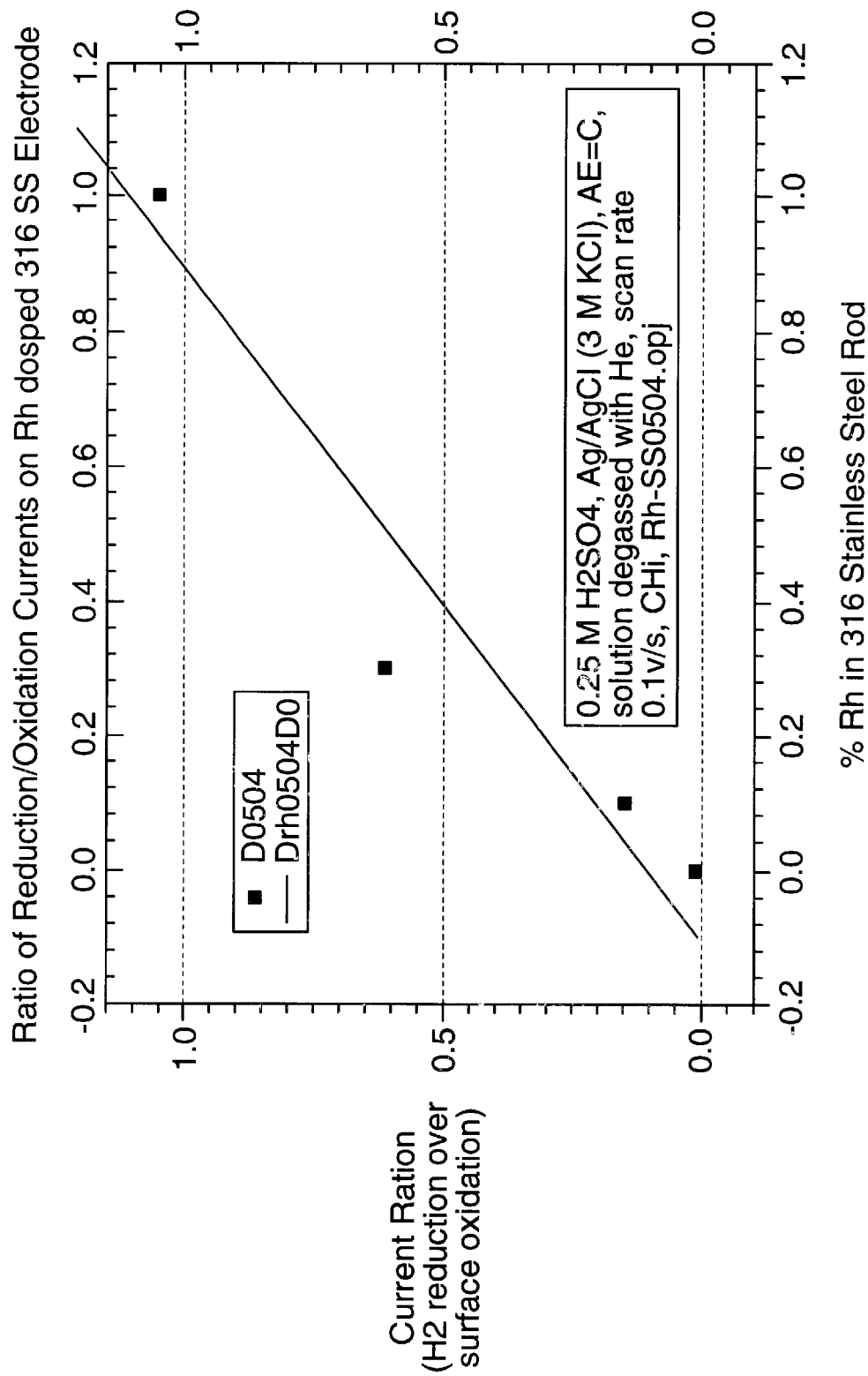
FIG. 17 is a plot of the relationship between Rh concentration and current ratio of reduction to oxidation in 0.25M $H_2SO_4$ at 25° C.

The data for Pt alloys and Rh alloys are summarized in FIGS. 16 and 17, respectively. FIGS. 16 and 17 are plotted by comparing the current ratio of hydrogen reduction to surface oxidation. The linear relationship between the noble metal concentration on the metal surface and the current ratio clearly shown in FIGS. 16 and 17.

Figure 18:
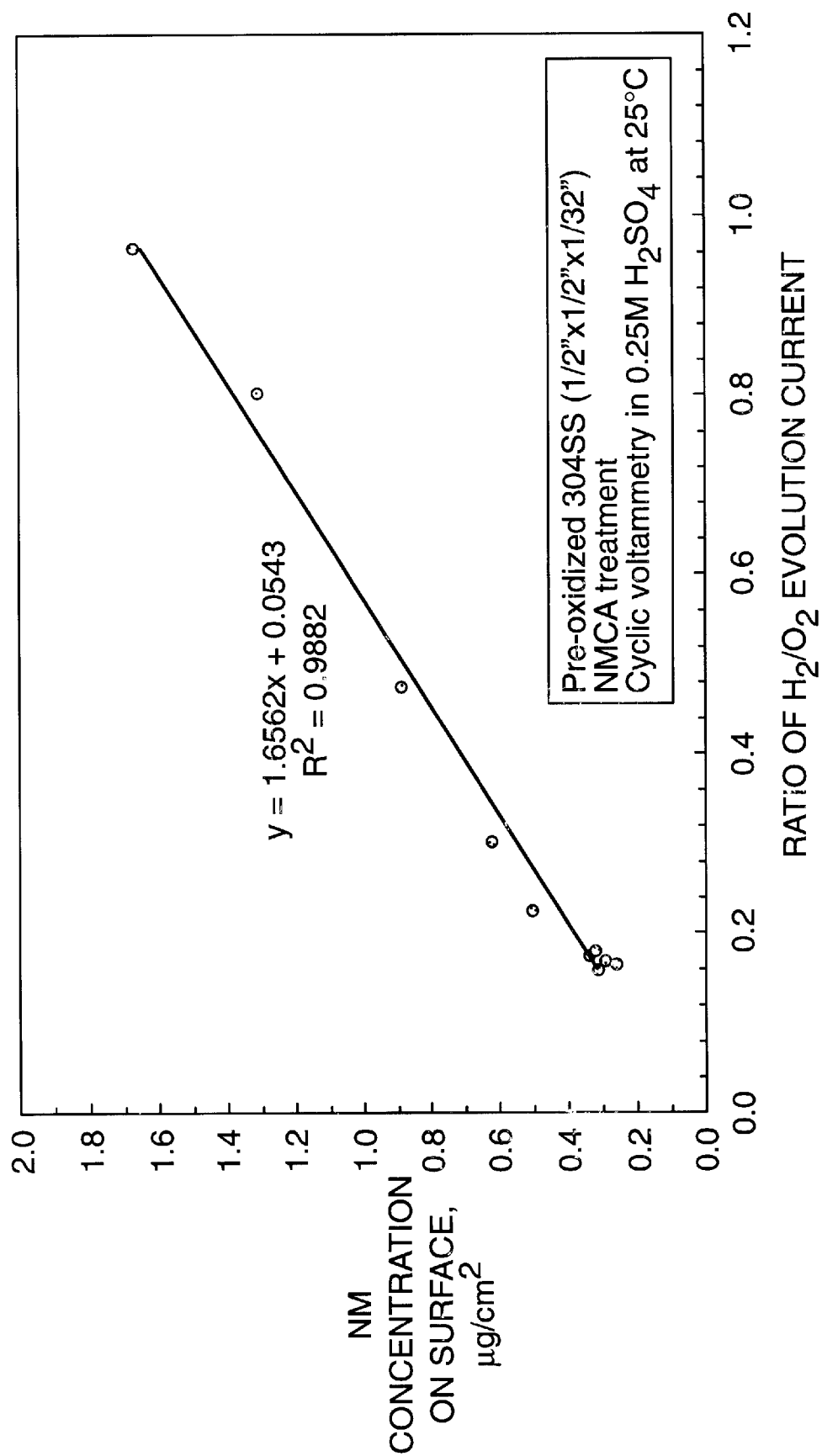
FIG. 18 is a plot of the relationship between total Pt/Rh concentration on the surface and current ratio of reduction to oxidation in 0.25M $H_2SO_4$ at 25° C.

The CV test was also performed on a 304 stainless steel sample treated by NMCA. The relationship between the current ratio and the Pt/Rh concentration on the surface is shown in FIG. 18. The Pt/Rh concentration on the surface was achieved by injecting the desired concentrations of noble metal chemicals—Pt as $Na_2Pt(OH)_6$ and Rh as $Na_3Rh(NO_2)_6$. The Pt and Rh concentrations on the surface after noble metal doping were also measured by the inductively coupled plasma mass spectroscopy (ICP-MS). It is evident that the presence of noble metals on the surface changes the oxidation and reduction kinetics.

While various embodiments are described herein, it will be appreciated from the specification that various combinations of elements, variations or improvements therein may be made by those skilled in the art, and are within the scope of the invention. For example, the system and method of the present invention can be used to determine the concentration of noble metals other than platinum or rhodium in BWR water and components. Among such noble metals are iridium, osmium, and palladium. The use of other electrochemical methods, such as LSV (linear sweep Voltametry), ASV (anodic stripping voltametry), DPA (differential pulse amperometry), and SWV (square wave voltametry) to determine evolution currents is also within the scope of the invention. Finally, the use of other calculational methods to determine noble metal concentrations is contemplated as well.

What is claimed is:

1. A system for determining a noble metal concentration in a collection sample, said collection sample having a surface and at least one noble metal disposed thereon, said noble metal concentration being representative of a first concentration of said noble metal in one of a volume of water and a surface of a solid component exposed to said volume of water, said system comprising:
    a) at least one standard having a standard surface and a predetermined concentration of said noble metal disposed thereon;
    b) an electrolyte bath for immersing one of said collection sample and said standard therein;
    c) an auxiliary electrode electrically connectable to one of said standard and said collection sample, said auxiliary electrode being immersible in said electrolyte bath;
    d) a power source electrically connectable to a reference electrode and one of said standard and said collection sample, said reference electrode being immersible in said electrolyte bath;
    wherein said power source is capable of providing a potential across said reference electrode and one of said collection sample and said standard, and
    e) a current measurement device capable of measuring a current passing between said auxiliary electrode and one of said collection sample and said standard,
        wherein said noble metal concentration in said collection sample is determined relative to said predetermined concentration in said standard by comparing a sample current passing through said collection sample to a standard current passing through said standard.

2. The system of claim 1, wherein said electrolyte bath is an acid bath capable of receiving at least one of said collection sample and said standard.

3. The system of claim 2, wherein said acid bath is an aqueous solution comprising an inorganic acid and water.

4. The system of claim 3, wherein said inorganic acid is an acid selected from the group consisting of nitric and sulfuric acid.

5. The system of claim 1, wherein said power source comprises a potentiostat.

6. The system of claim 1, wherein said current measurement device is an ammeter.

7. The system of claim 1, wherein said collection sample and said standard are formed from a material selected from the group consisting of carbon steel, low-alloy steel, stainless steel, and nickel-base alloys.

8. The system of claim 7, wherein said collection sample is insertable in a recirculating water loop of a boiling water nuclear reactor.

9. The system of claim 8, wherein said collection sample is a tubular section.

10. The system of claim 1, wherein said collection sample is a graphite electrode.

11. The system of claim 1, wherein said noble metal is a metal selected from the group consisting of platinum, rhodium, palladium, osmium, iridium, and combinations thereof.

12. The system of claim 1, wherein said volume of water is a volume of feed water for a boiling water reactor.

13. A cyclic voltametric apparatus for determining a noble metal concentration, wherein said noble metal concentration is determined by measuring a current produced by formation of one of hydrogen and oxygen in the presence of at least one noble metal, said cyclic voltametric apparatus comprising:

a) an electrode having a surface and said noble metal disposed thereon, an auxiliary electrode electrically connectable to said electrode, and a reference electrode. each of said electrode, said auxiliary electrode, and said reference electrode being immersible in an electrolyte bath;

b) a means for providing a potential between said reference electrode and said electrode and cyclically varying said potential between at least two predetermined potentials relative to said reference electrode;

c) a means for measuring a current passing between said electrode and said auxiliary electrode, wherein a hydrogen current produced by formation of hydrogen and an oxygen current produced by formation of oxygen are measured by said current measurement device during at least one reversible cyclic application of said potential between a first potential at which hydrogen forms and a second potential at which oxygen forms; and d) a means for determining the noble metal concentration from said current.

14. The cyclic voltametric apparatus of claim 13, wherein said means for measuring current is an ammeter.

15. The cyclic voltametric apparatus of claim 13, wherein said electrode comprises a material selected form the group consisting of carbon steel, low-alloy steel, stainless steel, and nickel-base alloys.

16. The cyclic voltametric apparatus of claim 13, wherein said auxiliary electrode is a carbon electrode.

17. The cyclic voltametric apparatus of claim 13, wherein said reference electrode is an electrode selected from the group consisting of a Ag|AgCl electrode, a Hg|HgO electrode, a saturated calomel electrode, and a platinum electrode.

18. The cyclic voltametric apparatus of claim 13, wherein said means for providing said potential and cyclically varying, said potential comprises a power source electrically connectable to each of said electrode and reference electrode.

19. A system for determining a noble metal concentration in a collection sample, said collection sample having a surface and at least one noble metal disposed thereon, said noble metal concentration being representative of a first concentration of said noble metal in one of a volume of water in a boiling water nuclear reactor and a surface of a solid component in said boiling water nuclear reactor that is exposed to said volume of water, said system comprising:

a) at least one standard having a standard surface and a predetermined concentration of said noble metal disposed thereon;

b) an electrolyte bath for immersing one of said collection sample and said standard therein, said electrolyte bath comprising an inorganic acid;

c) an auxiliary electrode, said auxiliary electrode being electrically connectable to one of said standard and said collection sample, and a reference electrode, each of said auxiliary electrode and said reference electrode being immersible in said electrolyte bath;

d) a power source electrically connectable to each of said reference electrode and one of said collection sample and said standard, said power source being capable of providing a potential between said reference electrode and one of said collection sample and said standard and cyclically varying said potential between at least two predetermined potentials relative to said reference electrode; and e) a current measurement device capable of measuring a current passing between said auxiliary electrode and one of said collection sample and said standard, wherein a hydrogen current produced by formation of hydrogen in said electrolyte bath and an oxygen current produced by formation of oxygen in said electrolyte bath are measured by said current measurement device during at least one reversibly cyclic variation of said potential between a first potential at which hydrogen forms and a second potential at which oxygen forms, and wherein said noble metal concentration in said collection sample is determined relative to said predetermined concentration by comparing a collection sample hydrogen current and a collection sample oxygen current measured for said collection sample to a standard hydrogen current and a standard oxygen current measured for said standard.

20. The system of claim 19, wherein said electrolyte bath is an aqueous solution comprising an inorganic acid and water.

21. The system of claim 20, wherein said inorganic acid is an acid selected from the group consisting of nitric acid and sulfuric acid.

22. The system of claim 19, wherein said power source comprises a potentiostat.

23. The system of claim 19, wherein said current measurement device is an ammeter.

24. The system of claim 19, wherein said collection sample and said standard are formed from a material selected from the group consisting of carbon steel, low-alloy steel, stainless steel, and nickel-base alloys.

25. The system of claim 24, wherein said collection sample is insertable in a recirculating water loop of a boiling water reactor.

26. The system of claim 25, wherein said collection sample is a tubular section.

27. The system of claim 19, wherein said noble metal is a metal selected from the group consisting of platinum, rhodium, palladium, osmium, iridium, and combinations thereof.

28. The system of claim 19, wherein said volume of water is a volume of feed water for said boiling water nuclear reactor.

29. The system of claim 19, wherein said auxiliary electrode is a carbon electrode.

30. The system of claim 19, wherein said reference electrode is an electrode selected from the group consisting of a Ag|AgCl electrode, a Hg|HgO electrode, a saturated calomel electrode, and a platinum electrode.

31. A method for determining a noble metal concentration in a collection sample, the collection sample containing at least one noble metal in a concentration that is representative of a noble metal concentration in one of a volume of water and a surface of a solid component exposed to the volume of water, the method comprising the steps of:

a) immersing the collection sample into an electrolyte solution;

b) connecting the collection sample to an auxiliary electrode;

c) connecting the collection sample and a reference electrode to a power source;

d) applying a potential between the collection sample and the reference electrode;

e) measuring a current passing between the auxiliary electrode and the collection sample;

f) providing at least one standard having a predetermined concentration of the noble metal;

g) immersing the standard into a second electrolyte solution;

h) connecting the standard to an auxiliary electrode;

i) connecting the standard and a reference electrode to a power source;

j) applying a potential between the standard and the reference electrode;

k) measuring a current passing between the auxiliary electrode and the standard; and l) comparing the current passing through the collection sample to the current passing through the standard, thereby determining the concentration of noble metals present in the collection sample relative to the predetermined concentration of noble metals present in the standard.

32. The method of claim 31, wherein the step of immersing the collection sample into an electrolyte solution comprises immersing the collection sample into a bath comprising a liquid selected from the group consisting of an acid solution, a neutral solution, and a basic solution.

33. The method of claim 31, wherein the step of applying a potential between the collection sample and the reference electrode further includes reversibly cycling the potential between a first predetermined potential and a second predetermined potential, and wherein the step of applying a potential between the standard and the reference electrode further includes reversibly cycling the potential between the first predetermined potential and the second predetermined potential.

34. The method of claim 33, wherein the first predetermined potential is the potential for the reduction of $H^+$ to form $H_2$ and the second predetermined potential is the potential for the decomposition of water to form $O_2$.

35. The method of claim 34, wherein the step of measuring a current passing through each of the collection sample and the standard further comprises measuring a first current in each of the collection sample and the standard at the first predetermined potential, and measuring a second current in each of the standard and collection sample at the second predetermined potential, wherein the first current is proportional to the rate of evolution of $H_2$ and the second current is proportional to the rate of evolution of $O_2$.

36. The method of claim 35, wherein the step of comparing the current passing through the collection sample to the current passing through the standard comprises the steps of:

a) calculating a sample ratio, the sample ratio being the ratio of the first current measured for the collection sample to the second current obtained for the collection sample;

b) calculating a standard ratio, the standard ratio being the ratio of the first current measured for the standard to the second current obtained for the standard; and c) dividing the sample ratio by the standard ratio to obtain a fraction, the fraction representing the concentration of the noble metal in the collection sample relative to the noble metal concentration in the standard.

37. A method of determining a noble metal concentration in a collection sample that is representative of a noble metal concentration in one of a volume of water circulated through a nuclear reactor and a surface of a nuclear reactor component exposed to the volume of water, the method comprising the steps of:

a) providing at least one collection sample, b) exposing the collection sample to the volume of water;

c) immersing the collection sample into an electrolyte solution;

d) connecting the collection sample to an auxiliary electrode;

e) connecting the collection sample and a reference electrode to a power source;

f) applying a potential between the collection sample and the reference electrode;

g) measuring a current passing between the auxiliary electrode and the collection sample;

h) providing at least one standard having a predetermined concentration of the noble metal;

i) immersing the standard into a second electrolyte solution;

j) connecting the standard to an auxiliary electrode;

k) connecting the standard and a reference electrode to a power source;

l) applying a potential between the standard and the reference electrode;

m) measuring a current passing between the auxiliary electrode and the standard; and n) comparing the current passing through the collection sample to the current passing through the standard, thereby determining the concentration of noble metals present in the collection sample relative to the predetermined concentration of noble metals present in the standard.

38. The method of claim 37, wherein the step of providing at least one collection sample further comprises:

a) placing the collection sample in a circulation path within the nuclear reactor through which the volume of water passes;

b) exposing the collection sample to the volume of water for a predetermined time period; and c) removing the collection sample from the circulation path.

39. The method of claim 37, wherein the step of immersing the collection sample into an electrolyte solution comprises immersing the collection sample into a bath comprising a liquid selected from the group consisting of an acid solution, a neutral solution, and a basic solution.

40. The method of claim 37, wherein the step of applying a potential between the collection sample and the reference electrode further includes reversibly cycling the potential between a first predetermined potential and a second predetermined potential, and wherein the step of applying a potential between the standard and the reference electrode further includes reversibly cycling the potential between the first predetermined potential and the second predetermined potential.

41. The method of claim 40, wherein the first predetermined potential is the potential for the reduction of $H^+$ to form $H_2$ and the second predetermined potential is the potential for the decomposition of water to form $O_2$.

42. The method of claim 41, wherein the step of measuring a current passing through each of the collection sample and the standard further comprises measuring a first current in each of the collection sample and the standard at the first predetermined potential, and measuring a second current in each of the collection sample and the standard at the second predetermined potential, wherein the first current is proportional to the rate of evolution of $H_2$ and the second. current is proportional to the rate of evolution of $O_2$.

43. The method of claim 42, wherein the step of comparing the current passing through the collection sample to the current passing through the standard comprises the steps of:

a) calculating a sample ratio, the sample ratio being the ratio of the first current measured for the collection sample to the second current obtained for the collection sample;

b) calculating a standard ratio, the standard ratio being the ratio of the first current measured for the standard to the second current obtained for the standard; and c) dividing the sample ratio by the standard ratio to obtain a fraction, the fraction representing the concentration of the noble metal in the collection sample relative to the noble metal concentration in the standard.

* * * * *